United States Patent
Kaku et al.

(10) Patent No.: US 9,629,527 B2
(45) Date of Patent: Apr. 25, 2017

(54) ENDOSCOPE SYSTEM, PROCESSOR DEVICE OF ENDOSCOPE SYSTEM, AND IMAGE PROCESSING METHOD

(71) Applicant: FUJIFILM Corporation, Tokyo (JP)

(72) Inventors: Toshihiko Kaku, Ashigarakami-gun (JP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 406 days.

(21) Appl. No.: 14/322,670

(22) Filed: Jul. 2, 2014

(65) Prior Publication Data

US 2014/0316195 A1  Oct. 23, 2014

Related U.S. Application Data

(63) Continuation of application No. PCT/JP2013/050359, filed on Jan. 11, 2013.

(30) Foreign Application Priority Data

Jan. 25, 2012 (JP) .................................. 2012-013316

(51) Int. Cl.
*A61B 1/04* (2006.01)
*A61B 1/06* (2006.01)
(Continued)

(52) U.S. Cl.
CPC ........ *A61B 1/0638* (2013.01); *A61B 1/00009* (2013.01); *A61B 1/063* (2013.01);
(Continued)

(58) Field of Classification Search
USPC ................................................ 600/104, 160
See application file for complete search history.

(56) References Cited

U.S. PATENT DOCUMENTS 9,167,960 B2 * 10/2015 Yamaguchi .......... A61B 1/0638
2003/0191368 A1 * 10/2003 Wang ................. A61B 1/00009
600/160
(Continued)

FOREIGN PATENT DOCUMENTS

JP    2011-36361 A    2/2011
JP    2011-98088 A    5/2011
(Continued)

OTHER PUBLICATIONS

Japanese Notice of Reasons for Rejection dated Apr. 22, 2015, for Japanese Application No. 2012-013316 with the English translation.
(Continued)

*Primary Examiner* — John P Leubecker
*Assistant Examiner* — Arnaldo Torres Diaz
(74) *Attorney, Agent, or Firm* — Birch, Stewart, Kolasch & Birch, LLP

(57) ABSTRACT

Broadband light BB and narrowband light NB are simultaneously irradiated to a subject. A blue signal B, a green signal G, and a red signal R are obtained by imaging the subject using a color CCD 33. A base image is generated from the signals B, G, and R of three colors. A B/G image having a B/G ratio is generated. A superficial blood vessel extraction image is obtained by extracting a pixel, in which the B/G ratio is equal to or less than a boundary value Ls between the mucous membrane and the superficial blood vessel, from the B/G image. A medium-deep blood vessel extraction image is obtained by extracting a pixel, in which the B/G ratio is equal to or greater than a boundary value Ld between the mucous membrane and the medium-deep blood vessel. The boundary values Ls and Ld differ depending on each observation mode.

20 Claims, 19 Drawing Sheets

(51) Int. Cl.
  *A61B 1/00* (2006.01)
  *G06T 5/50* (2006.01)
(52) U.S. Cl.
  CPC .............. *G06T 5/50* (2013.01); *A61B 1/0646* (2013.01); *A61B 1/0653* (2013.01); *G06T 2207/10024* (2013.01); *G06T 2207/10068* (2013.01); *G06T 2207/20212* (2013.01); *G06T 2207/30004* (2013.01); *G06T 2207/30101* (2013.01)

(56) References Cited

U.S. PATENT DOCUMENTS

| | | | |
|---|---|---|---|
| 2006/0198551 A1* | 9/2006 | Abe | A61B 1/00009 382/128 |
| 2007/0019846 A1* | 1/2007 | Bullitt | G06T 7/0014 382/128 |
| 2007/0153542 A1* | 7/2007 | Gono | A61B 1/0638 362/574 |
| 2008/0281154 A1* | 11/2008 | Gono | A61B 1/0638 600/109 |
| 2008/0294105 A1* | 11/2008 | Gono | A61B 1/0638 604/109 |
| 2009/0040298 A1* | 2/2009 | Yamazaki | A61B 1/0638 348/68 |
| 2011/0034770 A1 | 2/2011 | Endo et al. | |
| 2011/0077462 A1 | 3/2011 | Saitou et al. | |
| 2011/0112362 A1 | 5/2011 | Minetoma | |
| 2011/0172492 A1 | 7/2011 | Erikawa | |
| 2011/0237894 A1* | 9/2011 | Ozawa | A61B 1/043 600/168 |
| 2011/0237915 A1 | 9/2011 | Yamaguchi | |
| 2012/0010465 A1* | 1/2012 | Erikawa | A61B 1/05 600/109 |
| 2012/0327205 A1 | 12/2012 | Takahashi | |
| 2013/0289373 A1* | 10/2013 | Yamamoto | A61B 1/0638 600/339 |

FOREIGN PATENT DOCUMENTS

| | | |
|---|---|---|
| JP | 2011-135983 A | 7/2011 |
| JP | 2011-156339 A | 8/2011 |
| JP | 2011-200531 A | 10/2011 |
| JP | 2011-218135 A | 11/2011 |

OTHER PUBLICATIONS

International Search Report issued in PCT/JP2013/050359, dated Feb. 12, 2013.
Written Opinion of the International Searching Authority issued in PCT/JP2013/050359, dated Feb. 12, 2013.

* cited by examiner

ENDOSCOPE SYSTEM, PROCESSOR DEVICE OF ENDOSCOPE SYSTEM, AND IMAGE PROCESSING METHOD

CROSS-REFERENCE TO RELATED APPLICATIONS

This application is a Continuation of PCT International Application No. PCT/JP2013/050359 filed on Jan. 11, 2013, which claims priority under 35 U.S.C §119(a) to Japanese Patent Application No. 2012-013316 filed Jan. 25, 2012. Each of the above applications is hereby expressly incorporated by reference, in its entirety, into the present application.

BACKGROUND OF THE INVENTION

1. Field of the Invention

The present invention relates to an endoscope system capable of extracting blood vessels, such as superficial blood vessels and medium-deep blood vessels, in a subject, a processor device of an endoscope system, and an image processing method.

2. Description of the Related Art

In recent medical treatment, diagnosis or the like using an endoscope apparatus has been widely performed. As observation of the inside of a subject using an endoscope apparatus, not only normal observation using white light of broadband light as illumination light but also blood vessel enhancement observation, in which blood vessels in a subject are highlighted using narrowband light having a narrowband wavelength, has been performed.

In this blood vessel enhancement observation, determination regarding whether or not cancer is present from the shape of a blood vessel is performed. Types of blood vessels mainly include superficial blood vessels distributed on a living tissue surface and medium-deep blood vessels located below the superficial blood vessels. Depending on the purpose of diagnosis, diagnosis may be performed focusing on certain blood vessels. In this case, if blood vessels that are not the focus of observation are added in an endoscope image, there may be an interruption to diagnosis. For this reason, differentiating superficial blood vessels or medium-deep blood vessels from the image and displaying an image, which is obtained by extracting only blood vessels to be observed, on a monitor has been demanded.

Regarding the method of determining the depth of a blood vessel, JP2011-135983A discloses a method of performing determination of a superficial blood vessel when the hue of a narrowband image generated based on narrowband light in a specified wavelength region (415 nm, 540 nm) is 5 to 35 and performing determination as a medium-deep blood vessel when the hue is 170 to 200.

SUMMARY OF THE INVENTION

In observation of the body cavity using an endoscope, depending on a part, for example, in the esophagus and the stomach, the amount of return light from the subject may be different even if the esophagus and the stomach are illuminated with light having the same light amount. That is, the appearance or color of the blood vessel may change depending on the part If the color of the blood vessel changes in this way, it is difficult to reliably distinguish superficial blood vessels and medium-deep blood vessels with a blood vessel discrimination method based on the hue disclosed in JP2011-135983A.

The present invention has been made in view of the above-background, and it is an object of the present invention to provide an endoscope system capable of reliably extracting a plurality of types of blood vessels at different depths even if a part to be observed is changed, a processor device of an endoscope system, and an image processing method.

In order to achieve the above-described object, an endoscope system of the present invention includes: an illumination unit for irradiating a subject with illumination light including a blue component and a green component; an image signal acquisition unit for acquiring two or more color signals having different pieces of color information by receiving and imaging return light from the subject using an imaging element; a multi-color image generation unit for generating a multi-color image formed from calculated values obtained by performing predetermined calculation for each pixel using the two or more color signals; and a blood vessel extraction image generation unit for generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image.

Preferably, the blood vessel extraction image generation unit includes a plurality of calculated value tables, which are provided for each of the plurality of observation modes and store a correlation between a mucous membrane, the first layer blood vessel, and the second layer blood vessel of the subject and the calculated values, and a blood vessel extraction image generation section that generates at least one of the first layer blood vessel extraction image and the second layer blood vessel extraction image by performing blood vessel extraction processing using a calculated value table corresponding to the set observation mode.

Preferably, in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value. Preferably, the first and second boundary values differ depending on each calculated value table. Preferably, the plurality of observation modes are modes for improving visibility of a blood vessel in a predetermined part of the subject, and each of the observation modes is set for each predetermined part.

It is preferable to further include a blood vessel enhancement image or suppression image generation unit for generating a first layer blood vessel enhancement image or suppression image, in which the first layer blood vessel is enhanced or suppressed, using the first layer blood vessel extraction image or generating a second layer blood vessel enhancement image or suppression image, in which the second layer blood vessel is enhanced or suppressed, using the second layer blood vessel extraction image. It is preferable to further include a display unit for displaying at least one of the first layer blood vessel enhancement image or suppression image and the second layer blood vessel enhancement image or suppression image.

Preferably, the illumination unit simultaneously irradiates blue narrowband light and fluorescent light that is wavelength-converted by a wavelength conversion member using the blue narrowband light, as the illumination light, toward the subject, and the image signal acquisition unit images the subject, to which the blue narrowband light and the fluorescent light are irradiated simultaneously, using a color imaging element. As another implementation means, it is preferable that the illumination unit sequentially irradiate blue narrowband light and green narrowband light, as the illumination light, toward the subject and the image signal acquisition unit image the subject sequentially using a monochrome imaging element whenever the blue narrowband light and the green narrowband light are sequentially irradiated. Preferably, the color signals include a blue signal having information of a blue component and a green signal having information of a green component, and the multi-color image is a B/G image having a B/G ratio obtained by dividing the blue signal by the green signal for each pixel.

Other aspect of the present invention is a processor device of an endoscope system including an electronic endoscope that irradiates a subject with illumination light including a blue component and a green component and acquires two or more color signals having different pieces of color information by receiving and imaging return light from the subject using an imaging element. The processor device of an endoscope system includes: a multi-color image generation unit for generating a multi-color image formed from calculated values obtained by performing predetermined calculation for each pixel using the two or more color signals and a blood vessel extraction image generation unit for generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image.

Other aspect of the present invention is an image processing method performed in an endoscope system including an electronic endoscope that irradiates a subject with illumination light including a blue component and a green component and acquires two or more color signals having different pieces of color information by receiving and imaging return light from the subject using an imaging element. The image processing method includes: generating a multi-color image formed from calculated values obtained by performing predetermined calculation for each pixel using the two or more color signals; and generating at least one of a first layer blood vessel extraction image, which is obtained by extracting a first layer blood vessel at a specific depth from the multi-color image, and a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image.

According to the present invention, different blood vessel extraction processing is performed for each of a plurality of observation modes. Therefore, even if a part to be observed is changed, a plurality of types of blood vessels at different depths can be reliably extracted by performing switching to the observation mode corresponding to the part.

DESCRIPTION OF THE PREFERRED EMBODIMENTS

Figure 1:
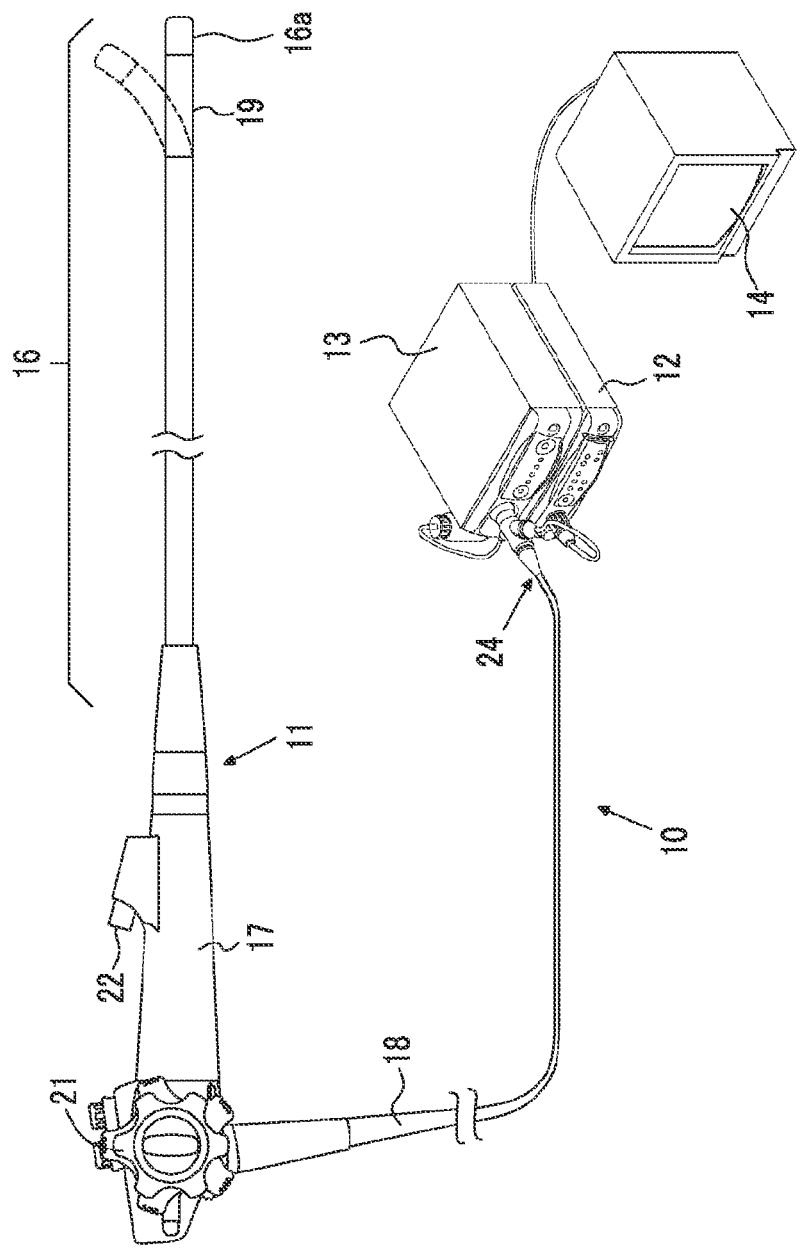
FIG. 1 is an external view of an endoscope system.

As shown in FIG. 1, an electronic endoscope system 10 of a first embodiment includes an electronic endoscope 11 that images the inside of a subject, a processor device 12 that generates an endoscope image based on a signal obtained by imaging, a light source device 13 (a form of an illumination unit) that generates light for illuminating the subject, and a monitor 14 that displays an endoscope image. The electronic endoscope 11 includes a flexible insertion unit 16 that is inserted into the body cavity, an operating unit 17 provided at the proximal end of the insertion unit 16, and a universal code 18 that makes a connection between the operating unit 17 and the processor device 12 and the light source device 13.

The electronic endoscope system 10 has a function of generating a superficial blood vessel enhancement image or suppression image, in which a superficial blood vessel of a subject is enhanced/suppressed, and a medium-deep blood vessel enhancement image or suppression image, in which a medium-deep superficial blood vessel is enhanced/suppressed. Which blood vessel enhancement image or suppression image is to be generated is determined by the operation of a superficial layer and medium-deep layer selection SW 28 (refer to FIG. 2). In endoscopic observation, the appearance of the blood vessel changes with each part, such as the stomach, colon, and esophagus. Accordingly, there is a function of correcting this. The appearance of the blood vessel changes with the ratio P between a blue component (B component) and a green component (G component) of return light (reflected light or the like) that is returned from the subject. Here, it is assumed that the observation mode of a part for which the percentage of the B component is approximately the same as the percentage of the G component is a first observation mode, the observation mode of a part for which the percentage of the B component is larger than the percentage of the G component is a second observation mode, and the observation mode of a part for which the percentage of the G component is larger than the percentage of the B component is a third observation mode. The first to third observation modes can be switched when an operator operates an observation mode selection SW 29 according to a part to be observed (refer to FIG. 2).

A curved portion 19 obtained by connecting a plurality of curved pieces is formed at the distal end of the insertion unit 16. The curved portion 19 is curved in the horizontal and vertical directions by operating an angle knob 21 of the operating unit. A distal portion 16a including an optical system for imaging the body cavity and the like is provided at the distal end of the curved portion 19. The distal portion 16a is directed in a desired direction within the body cavity by the bending operation of the curved portion 19.

A connector 24 is attached to the universal code 18 on the side of the processor device 12 and the light source device 13. The connector 24 is a composite connector including a communication connector and a light source connector, and the electronic endoscope 11 is detachably connected to the processor device 12 and the light source device 13 through the connector 24.

Figure 2:
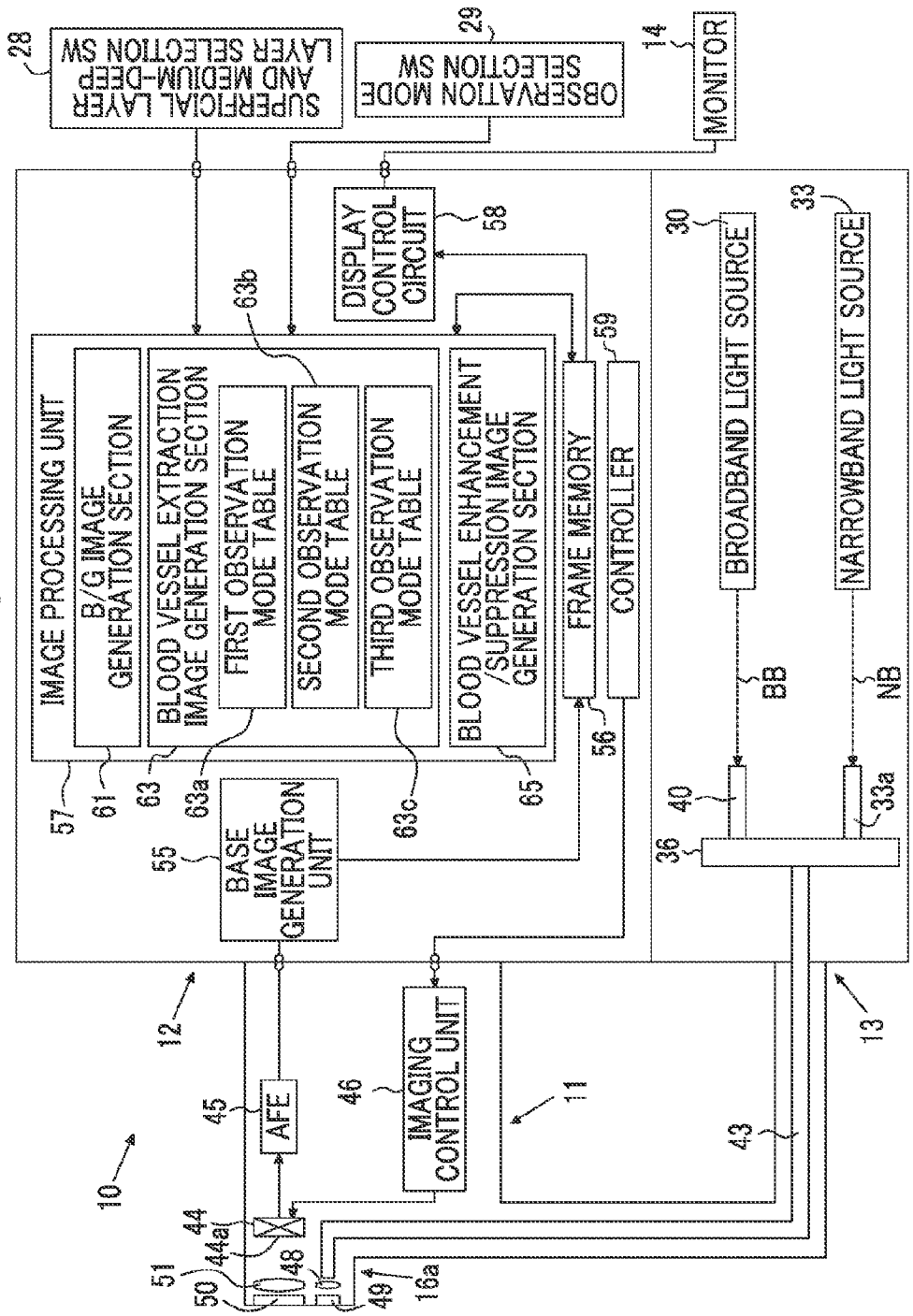
FIG. 2 is a block diagram showing the electrical configuration of an endoscope system of a first embodiment.
Figure 3:
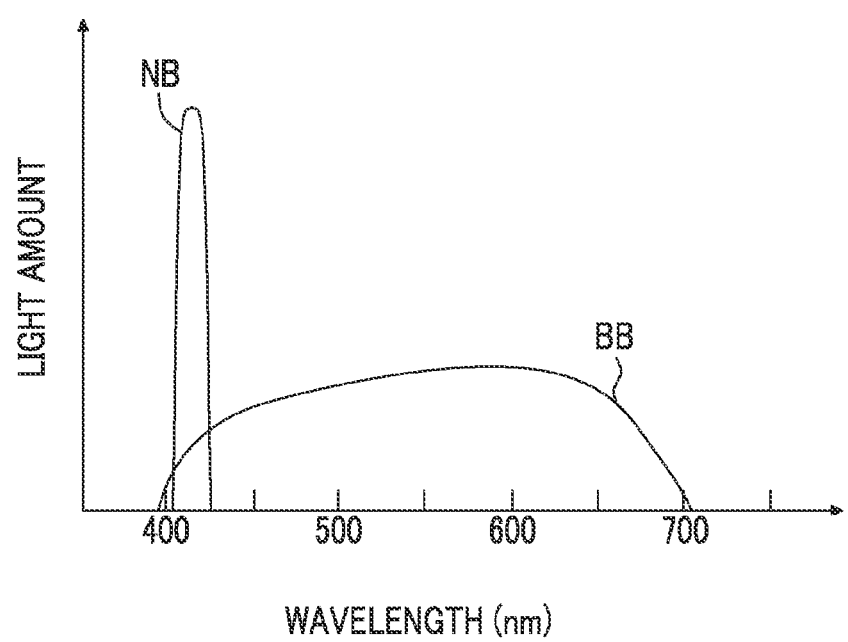
FIG. 3 is a graph showing the emission spectra of broadband light and narrowband light.
Figure 4:
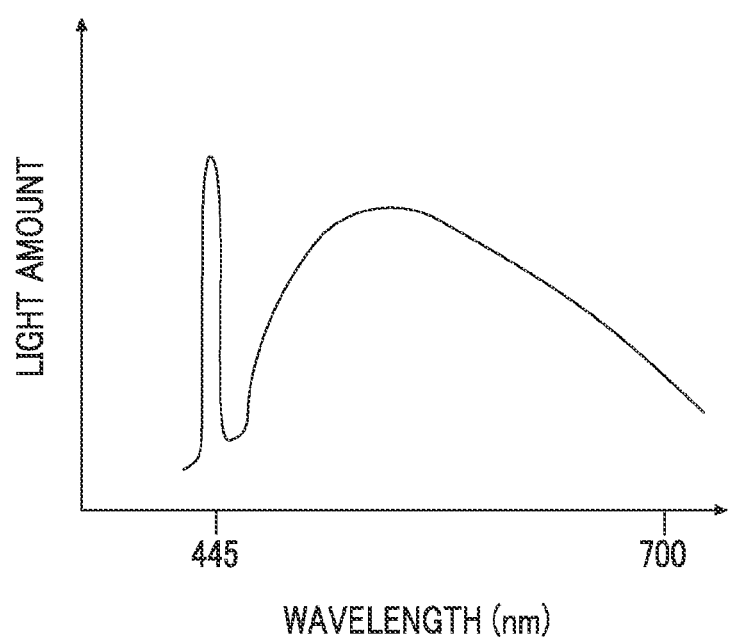
FIG. 4 is a graph showing the emission spectra of blue laser light and emitted excitation light that is excited and emitted by applying the blue laser light to a phosphor.

As shown in FIG. 2, the light source device 13 includes a broadband light source 30, a narrowband light source 33, and a coupler 36. As shown in FIG. 3, the broadband light source 30 generates broadband light BB in a wavelength range from the blue region to the red region (about 400 nm to 700 nm). The broadband light source 30 is always ON while the electronic endoscope 11 is used. The broadband light BB emitted from the broadband light source 30 is incident on a broadband optical fiber 40. As the broadband BB, not only white light of a xenon lamp or the like but also white light (refer to FIG. 4 for the emission spectrum), which is obtained by combining laser light having a center wavelength of 445 nm with emitted excitation light of 460 nm to 700 nm that is excited and emitted from a phosphor by the laser light, may be used.

The narrowband light source 33 is a light emitting diode (LED), a laser diode (LD), or the like. As shown in FIG. 3, the narrowband light source 33 generates narrowband light NB having a limited wavelength of 400±10 nm (center wavelength of 405 nm). The narrowband light NB emitted from the narrowband light source 33 is incident on a narrowband optical fiber 33a. In addition, the wavelength of the narrowband light NB is not limited to 400±10 nm (center wavelength of 405 nm). For example, narrowband light having a wavelength of 440±10 nm (center wavelength of 445 nm) may be used.

The coupler 36 connects a light guide 43 in the electronic endoscope 11 to the broadband optical fiber 40 and the narrowband optical fiber 33a. Therefore, both the broadband light BB and the narrowband light NB are simultaneously incident on the light guide 43.

The electronic endoscope 11 includes the light guide 43, a CCD 44, an analog processing circuit 45 (analog front end: AFE), and an imaging control unit 46. The light guide 43 is a large-diameter optical fiber, a bundle fiber, or the like, and the incidence end is inserted into the coupler 36 in the light source device and the exit end is directed toward an irradiation lens 48 provided in the distal portion 16a. The broadband light BB and the narrowband light NB guided by the light guide 43 are irradiated into the subject through the irradiation lens 48 and an illumination window 49 attached to the end surface of the distal portion 16a. The broadband light BB and the narrowband light NB reflected within the subject are incident on a condensing lens 51 through an observation window 50 attached to the end surface of the distal portion 16a.

The CCD 44 receives light from the condensing lens 51 through an imaging surface 44a, performs photoelectric conversion of the received light and accumulates signal charges, and reads the accumulated signal charges as an imaging signal. The read imaging signal is transmitted to an AFE 45. The CCD 44 is a color CCD, and pixels of three colors of a B pixel in which a color filter of B color is provided, a G pixel in which a color filter of G color is provided, and an R pixel in which a color filter of R color is provided are arrayed on the imaging surface 44a. A form of an image signal acquisition unit is configured to include the condensing lens 51, the CCD 44 having the imaging surface 44a, and the AFE 45.

Figure 5:
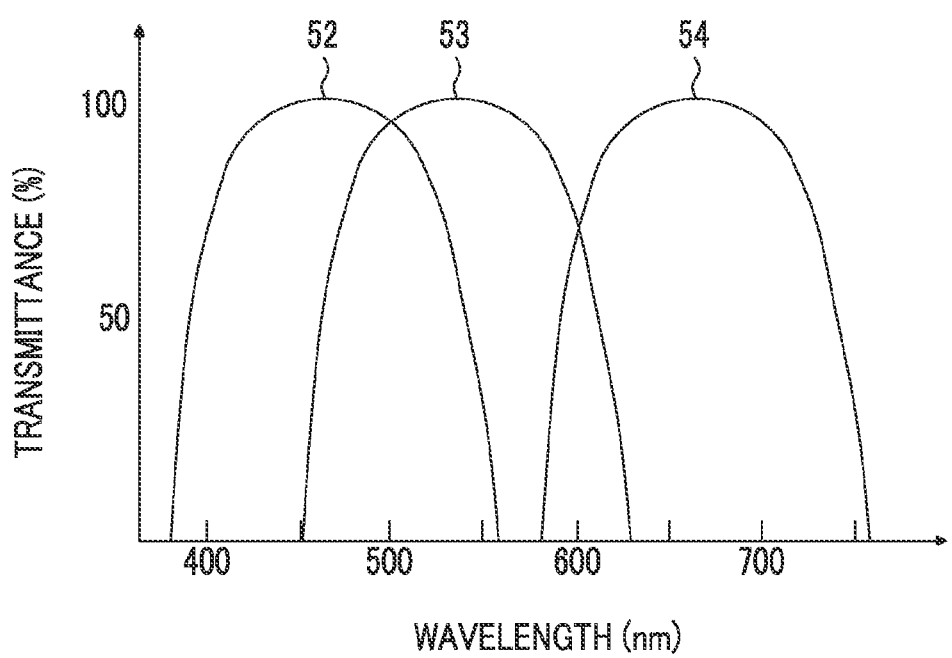
FIG. 5 is a graph showing the spectral transmittances of color filters of R, G, and B colors.

The color filters of B, G, and R colors have transmission distributions 52, 53, and 54, respectively, as shown in FIG. 5. When only the broadband light BB having a wavelength region of about 400 nm to 700 nm is incident on the CCD 44, the color filters of B, G, and R colors allow light having a wavelength corresponding to the transmission distributions 52, 53, and 54, of the broadband light BB, to be transmitted therethrough. Here, it is assumed that a signal photoelectrically converted by the R pixel is a red signal R, a signal photoelectrically converted by the G pixel is a green signal G, and a signal photoelectrically converted by the B pixel is a blue signal B.

The AFE 45 is configured to include a correlated double sampling circuit (CDS), an automatic gain control circuit (AGC), and an analog/digital converter (A/D) (all not shown). The CDS performs correlated double sampling processing on an imaging signal from the CCD 44 to remove noise caused by the driving of the CCD 44. The AGC amplifies an imaging signal from which noise has been removed by the CDS. The A/D converts an imaging signal amplified by the AGC into a digital imaging signal of a predetermined number of bits, and inputs the digital imaging signal to the processor device 12.

The imaging control unit 46 is connected to a controller 59 in the processor device 12, and transmits a driving signal to the CCD 44 when there is an instruction from the controller 59. The CCD 44 outputs an imaging signal to the AFE 45 at a predetermined frame rate based on the driving signal from the imaging control unit 46.

As shown in FIG. 2, the processor device 12 includes a base image generation unit 55, a frame memory 56, an image processing unit 57, and a display control circuit 58. The controller 59 controls each of the units. The base image generation unit 55 generates a base image by performing various kinds of signal processing on the blue signal B, the green signal G, and the red signal R output from the AFE 45 of the electronic endoscope. The generated base image is temporarily stored in the frame memory 56. The blue signal B, the green signal G, and the red signal R output from the AFE 45 are stored in the frame memory 56. The base image may be a normal observation image, which is obtained by using only the broadband light BB without using the narrowband light NB, or a pseudo color image, which is obtained by pseudo coloring of blood vessel function information, such as oxygen saturation.

The image processing unit 57 includes a B/G image generation section 61 (a form of a multi-color image generation unit), a blood vessel extraction image generation section 63, and a blood vessel enhancement image or suppression image generation section 65 (a form of a blood vessel enhancement image or suppression image generation unit). The B/G image generation section 61 generates a B/G image having a brightness ratio B/G (B/G ratio) between the blue signal B and the green signal G. Here, the B/G ratio indicates a brightness ratio of pixels at the same position between the blue signal B and the green signal G.

Figure 6:
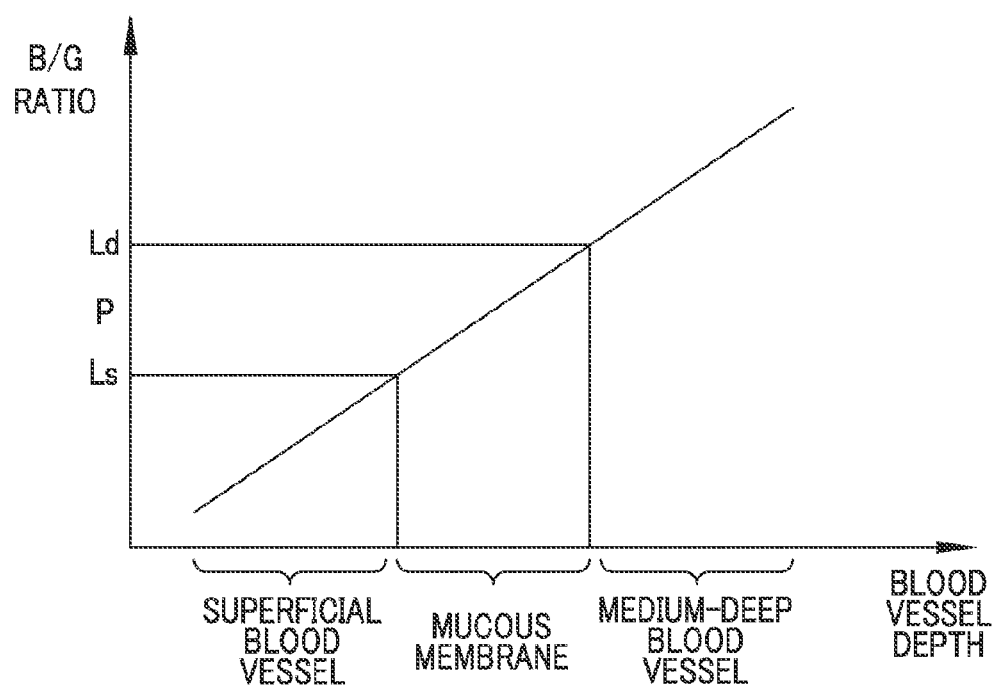
FIG. 6 is a graph showing the relationship between the blood vessel depth and the B/G ratio that is stored in a first observation mode table.

The blood vessel extraction image generation section 63 generates a superficial blood vessel extraction image by extracting the superficial blood vessel based on the B/G image, or generates a medium-deep blood vessel extraction image by extracting the medium-deep blood vessel based on the B/G image. The method of generating the blood vessel extraction images differs depending on which of the first to third observation modes is set. When the first observation mode is set, a superficial blood vessel extraction image or a medium-deep blood vessel extraction image is generated using a first observation mode table 63a. Correlation between the brightness ratio B/G and the blood vessel depth shown in FIG. 6 is stored in the first observation mode table 63a. This correlation is a proportional relationship in which the brightness ratio B/G (B/G ratio) increases as the blood vessel depth increases. In addition, a form of a blood vessel extraction image generation unit is configured to include a blood vessel extraction image generation section 63 and the first observation mode table 63a to a third observation mode table 63c.

Figure 7:
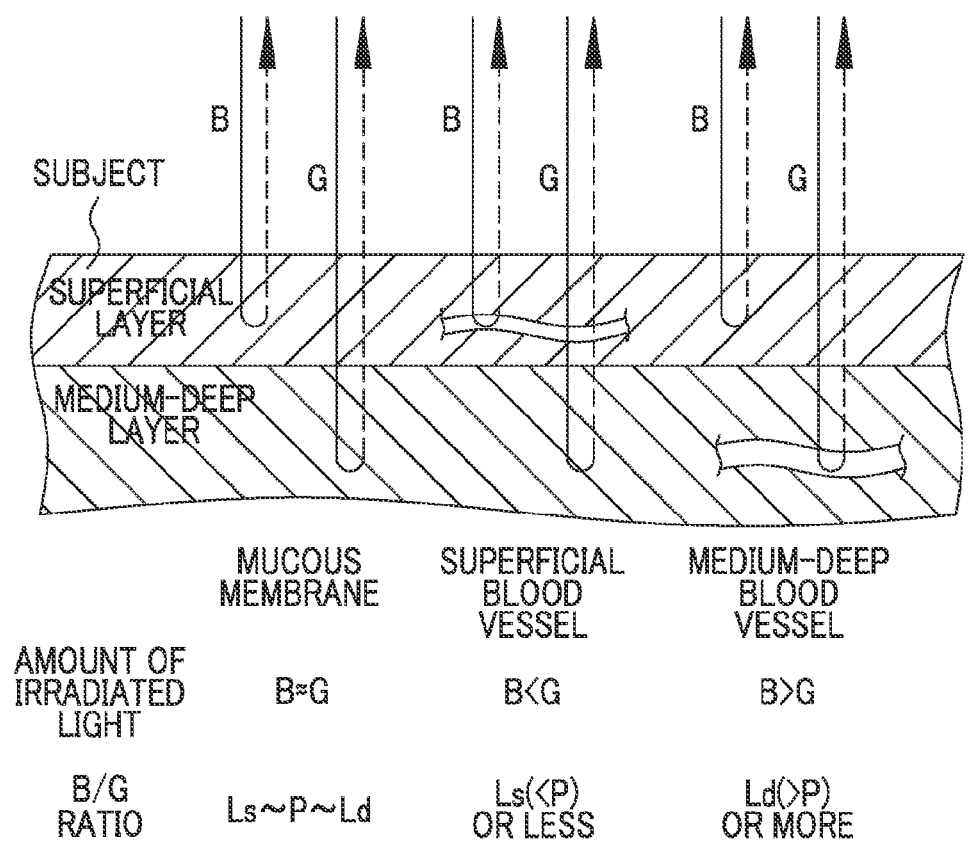
FIG. 7 is a diagram for explaining the B/G ratio of the mucous membrane, the superficial blood vessel, and the medium-deep blood vessel when return light, in which the ratio between the B and G components is approximately the same, is received.

In the first observation mode, the percentage of the blue wavelength component (B component) of return light from the subject is approximately the same as the percentage of the green wavelength component (G component) of the return light. Therefore, as shown in FIG. 7, when the illumination light is irradiated to the mucous membrane with no blood vessels, the ratio of the B and G components of the return light is approximately fixed. This is because there is no large light absorption in the mucous membrane. Assuming that the average B/G ratio in this case is P, the B/G ratio in the mucous membrane falls within a fixed range of "Ls to P to Ld". Here Ls is a lower limit of the B/G ratio of the mucous membrane in the first observation mode, and Ld is an upper limit of the B/G ratio of the mucous membrane in the first observation mode.

When illumination light is irradiated to a superficial blood vessel, the B component of the illumination light is largely absorbed by the superficial blood vessel, while the G component is not absorbed almost. For this reason, the B/G ratio is equal to or less than Ls in most cases. Therefore, it can be seen that the superficial blood vessel is projected to the pixel having a B/G ratio equal to or less than Ls (that is, Ls is a boundary value between the mucous membrane and the superficial blood vessel). On the other hand, when illumination light is irradiated to a medium-deep blood vessel, the G component of the illumination light is largely absorbed by the medium-deep blood vessel, while the B component is not absorbed almost. For this reason, the B/G ratio is equal to or greater than Ld in most cases. Therefore, it can be seen that the medium-deep blood vessel is projected to the pixel having a B/G ratio equal to or larger than Ld (that is, Ld is a boundary value between the mucous membrane and the medium-deep blood vessel).

Accordingly, when generating a superficial blood vessel extraction image in the first observation mode, only the pixel value of a pixel having a B/G ratio equal to or less than Ls is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld is extracted from the B/G image, and binarization processing for setting the pixel values of other pixels to 0 is performed.

Figure 8:
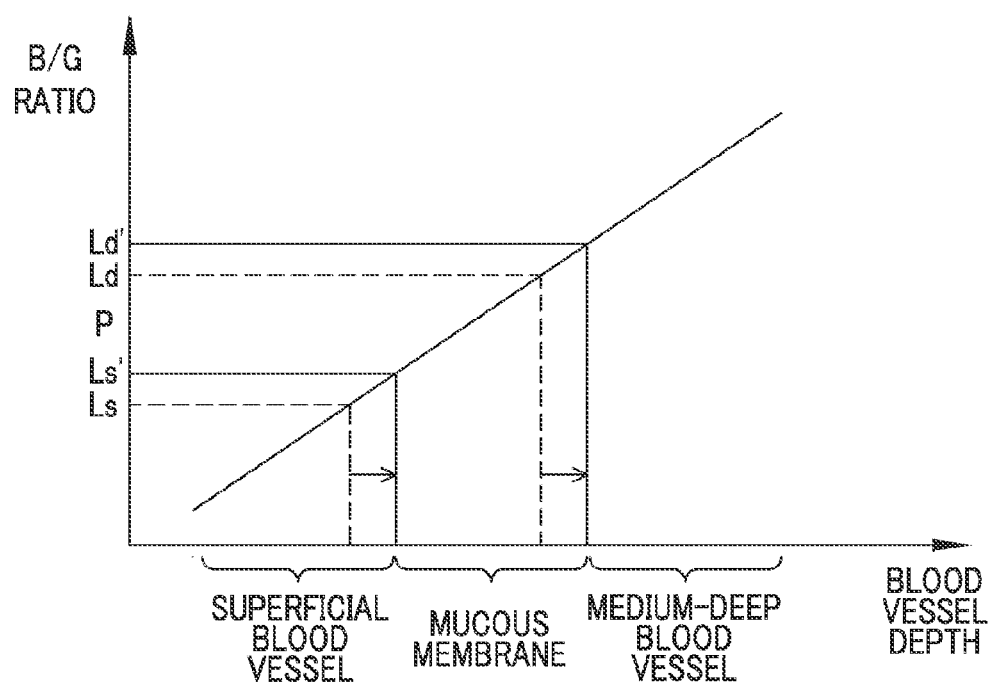
FIG. 8 is a graph showing the relationship between the blood vessel depth and the B/G ratio that is stored in a second observation mode table
Figure 9:
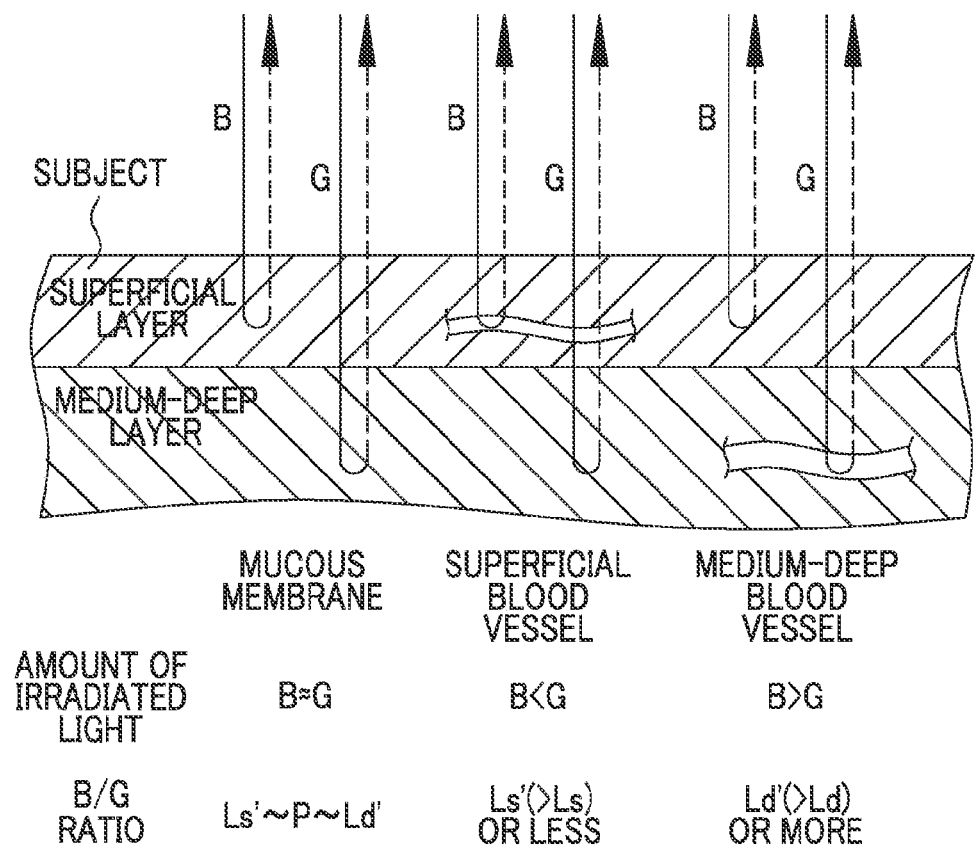
FIG. 9 is a diagram for explaining the B/G ratio of the mucous membrane, the superficial blood vessel, and the medium-deep blood vessel when return light, in which the percentage of the B component is larger than the percentage of the G component, is received.

When the second observation mode is set, a superficial blood vessel extraction image or a medium-deep blood vessel extraction image is generated using the second observation mode table 63b. As shown in FIG. 8, similar to the first observation mode table 63a, the second observation mode table 63b shows a proportional relationship in which the brightness ratio B/G (B/G ratio) increases as the blood vessel depth increases. In the second observation mode, as shown in FIG. 9, since the percentage of the blue wavelength component (B component) of return light from the subject is larger than the percentage of the green wavelength component (G component) of the return light, the B/G ratio is generally high. Accordingly, a boundary value Ls' between the mucous membrane and the superficial blood vessel is larger than the boundary value Ls in the first observation mode, and a boundary value Ld' between the mucous membrane and the medium-deep blood vessel is larger than the boundary value Ld in the first observation mode.

Therefore, when generating a superficial blood vessel extraction image in the second observation mode, only the pixel value of a pixel having a B/G ratio equal to or less than Ls' is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld' is extracted from the B/G image, and binarization processing for setting the pixel values of other pixels to 0 is performed.

Figure 10:
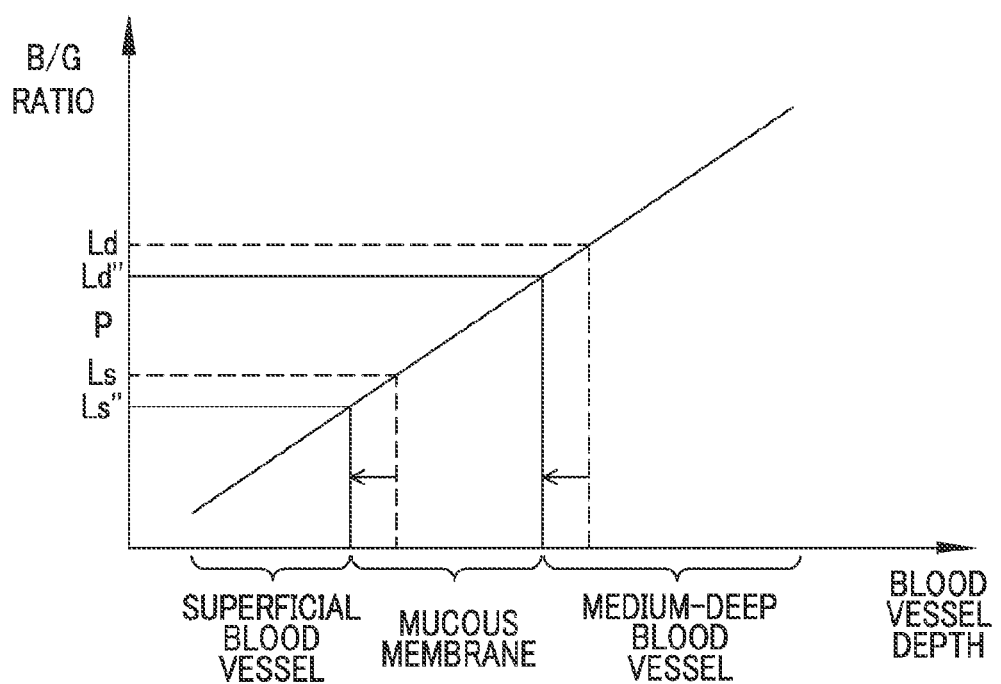
FIG. 10 is a graph showing the relationship between the blood vessel depth and the B/G ratio that is stored in a third observation mode table.
Figure 11:
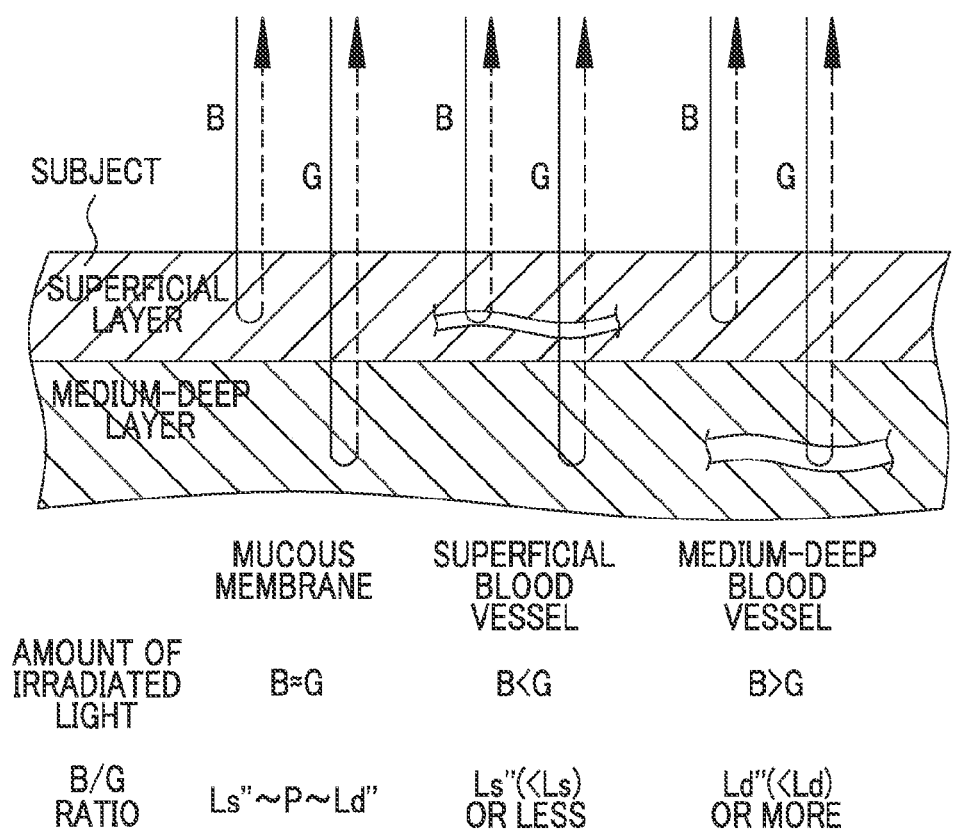
FIG. 11 is a diagram for explaining the B/G ratio of the mucous membrane, the superficial blood vessel, and the medium-deep blood vessel when return light, in which the percentage of the G component is larger than the percentage of the B component, is received.

When the third observation mode is set, a superficial blood vessel extraction image or a medium-deep blood vessel extraction image is generated using the third observation mode table 63c. As shown in FIG. 10, similar to the first observation mode table 63a, the third observation mode table 63c shows a proportional relationship in which the brightness ratio B/G (B/G ratio) increases as the blood vessel depth increases. In the third observation mode, as shown in FIG. 11, since the percentage of the green wavelength component (G component) of return light from the subject is larger than the percentage of the blue wavelength component (B component) of the return light, the B/G ratio is generally low. Accordingly, a boundary value Ls" between the mucous membrane and the superficial blood vessel is smaller than the boundary value Ls in the first observation mode, and a boundary value Ld" between the mucous membrane and the medium-deep blood vessel is smaller than the boundary value Ld in the first observation mode.

Therefore, when generating a superficial blood vessel extraction image in the third observation mode, only the pixel value of a pixel having a B/G ratio equal to or less than Ls" is extracted from the B/G image, and binarization processing for setting the pixel values of other pixels to 0 is performed. On the other hand, when generating a medium-deep blood vessel extraction image, only the pixel value of a pixel having a B/G ratio equal to or greater than Ld" is extracted from the B/G image, and binarization processing for setting the pixel values of other pixels to 0 is performed.

From diagnosis and the like until now, it has been found that the relationship of the average B/G ratio in each part of the esophagus, colon, and stomach is B/G ratio of esophagus>B/G ratio of colon>B/G ratio of stomach. Therefore, it is preferable to set the first observation mode when observing the colon, set the second observation mode when observing the esophagus, and set the third observation mode when observing the stomach, although this also depends on the purpose of diagnosis and other observation conditions.

The blood vessel enhancement image or suppression image generation section 65 generates a superficial blood vessel enhancement image or suppression image, in which a superficial blood vessel is enhanced (or suppressed), by combining the superficial blood vessel extraction image and the base image, and generates a medium-deep blood vessel enhancement image or suppression image, in which a medium-deep blood vessel is enhanced (or suppressed), by combining the medium-deep blood vessel extraction image and the base image. When enhancing the blood vessel a value obtained by increasing the pixel value of each pixel in the superficial blood vessel extraction image (or a medium-deep blood vessel extraction image several times is added to the pixel value of each pixel of the base image. When suppressing the blood vessel, a value obtained by increasing the pixel value of each pixel in the superficial blood vessel extraction image (or a medium-deep blood vessel extraction image) several times is subtracted from the pixel value of each pixel of the base image.

Figure 12:
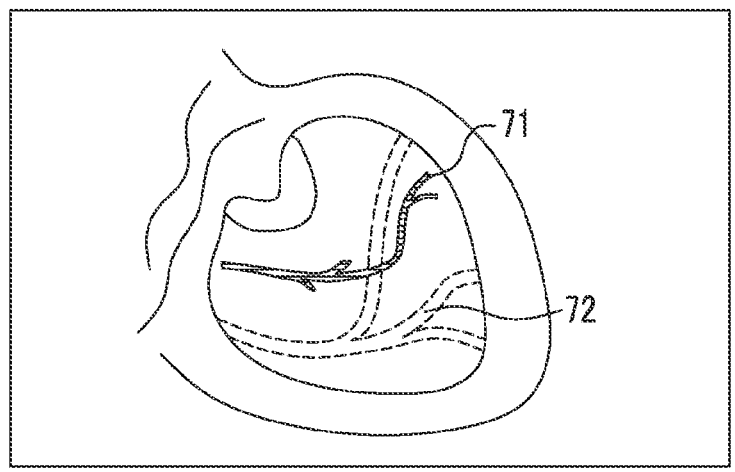
FIG. 12 is an image diagram showing an image in which the superficial blood vessel is enhanced and the medium-deep blood vessel is suppressed.
Figure 13:
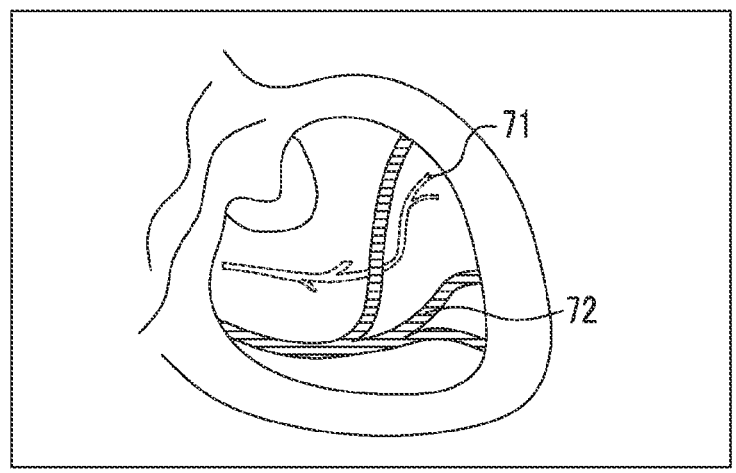
FIG. 13 is an image diagram showing an image in which the superficial blood vessel is suppressed and the medium-deep blood vessel is enhanced.

The display control circuit 58 displays the blood vessel enhancement image or suppression image on the monitor 14 (a form of a display unit). For example, as shown in FIG. 12, when a superficial blood vessel 71 extracted from the B/G image is enhanced on the blood vessel enhancement image or suppression image, diagnosis focusing on only the superficial blood vessel 71 is possible since the superficial blood vessel 71 is noticeable compared with a medium-deep blood vessel 72, In contrast, as shown in FIG. 13, when the medium-deep blood vessel 72 extracted from the B/G image is enhanced on the blood vessel enhancement image or suppression image, diagnosis focusing on only the medium-deep blood vessel 72 is possible since the medium-deep blood vessel 72 is noticeable compared with the superficial blood vessel 71.

As described above, by extracting only an image of the blood vessel to be observed from the B/G image and generating a blood vessel enhancement image or suppression image using the extracted blood vessel image, only the blood vessel portion to be observed can be reliably enhanced/suppressed without eliminating the information of portions other than the blood vessel, for example, the information of unevenness of a part to be observed. Therefore, since not only the blood vessel information but also a lot of information useful for diagnosis, such as unevenness of a part to be observed, can be provided to the user, it is possible to improve the diagnostic performance. In addition, since blood vessels are divided into the superficial blood vessel and the medium-deep blood vessel so as to be separately extracted and each of the superficial blood vessel and the medium-deep blood vessel is separately enhanced/ suppressed, diagnosis focusing on the superficial blood vessel or diagnosis focusing on the medium-deep blood vessel is possible.

Figure 14:
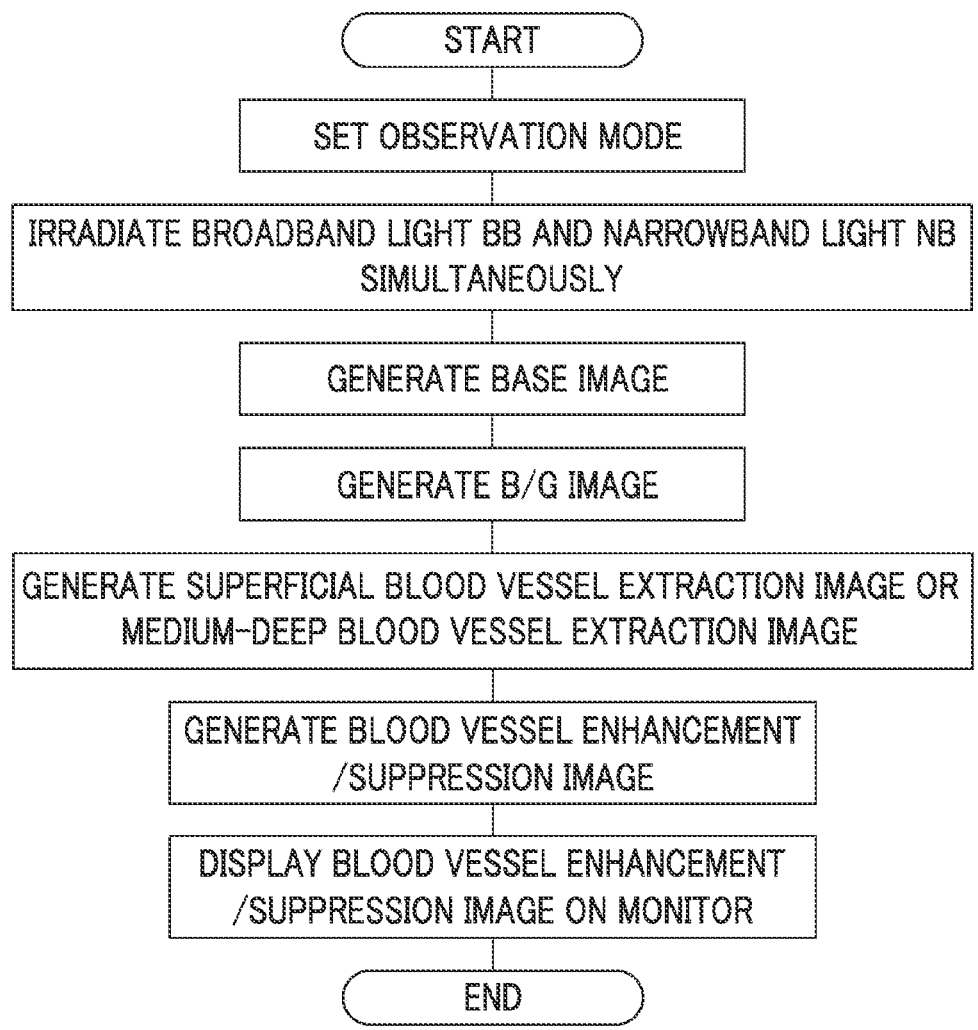
FIG. 14 is a flowchart showing the operation of one embodiment of the present invention.

Next, the operation of one embodiment of the present invention will be described with reference to the flowchart shown in FIG. 14. First, an observation mode corresponding to a part among the first to third observation modes is set. The broadband light BB and the narrowband light NB emitted from the light source device 13 are irradiated simultaneously into the subject through the light guide 43. Reflected light from the subject is imaged by the color CCD 44. A base image is generated from the blue signal B, the green signal G, and the red signal R obtained by this imaging. The generated base image, the blue signal B, the green signal G, and the red signal R are temporarily stored in the frame memory 56.

Then, the B/G image generation section 61 generates a B/G image having the brightness ratio B/G between the blue signal B and the green signal G. A superficial blood vessel extraction image is generated by extracting the superficial blood vessel from the B/G image, and a medium-deep blood vessel extraction image is generated by extracting the medium-deep blood vessel from the B/G image. An observation mode table corresponding to the set observation mode is used for the blood vessel extraction. If the blood vessel extraction image is generated, a blood vessel enhancement image or suppression image in which a superficial blood vessel (or a medium-deep blood vessel) is enhanced/suppressed is generated from the superficial blood vessel extraction image (or the medium-deep blood vessel extraction image) and the base image. The generated blood vessel enhancement image or suppression image is converted into a signal, which can be displayed on a monitor, by the display control circuit 58 and is then image-displayed on the monitor 14 as shown in FIG. 12 or 13.

In the first embodiment described above, the broadband light BB is emitted from the broadband light source 30 in the light source device 13. However, instead of this, fluorescent light may be emitted by providing a phosphor in the distal portion 16a of the electronic endoscope 11 and exciting the phosphor with excitation light from an excitation light source provided in the light source device 13. In this case, light obtained by combining fluorescent light and excitation light, which is not absorbed by the phosphor, is irradiated into the subject as the broadband light BB.

Figure 15:
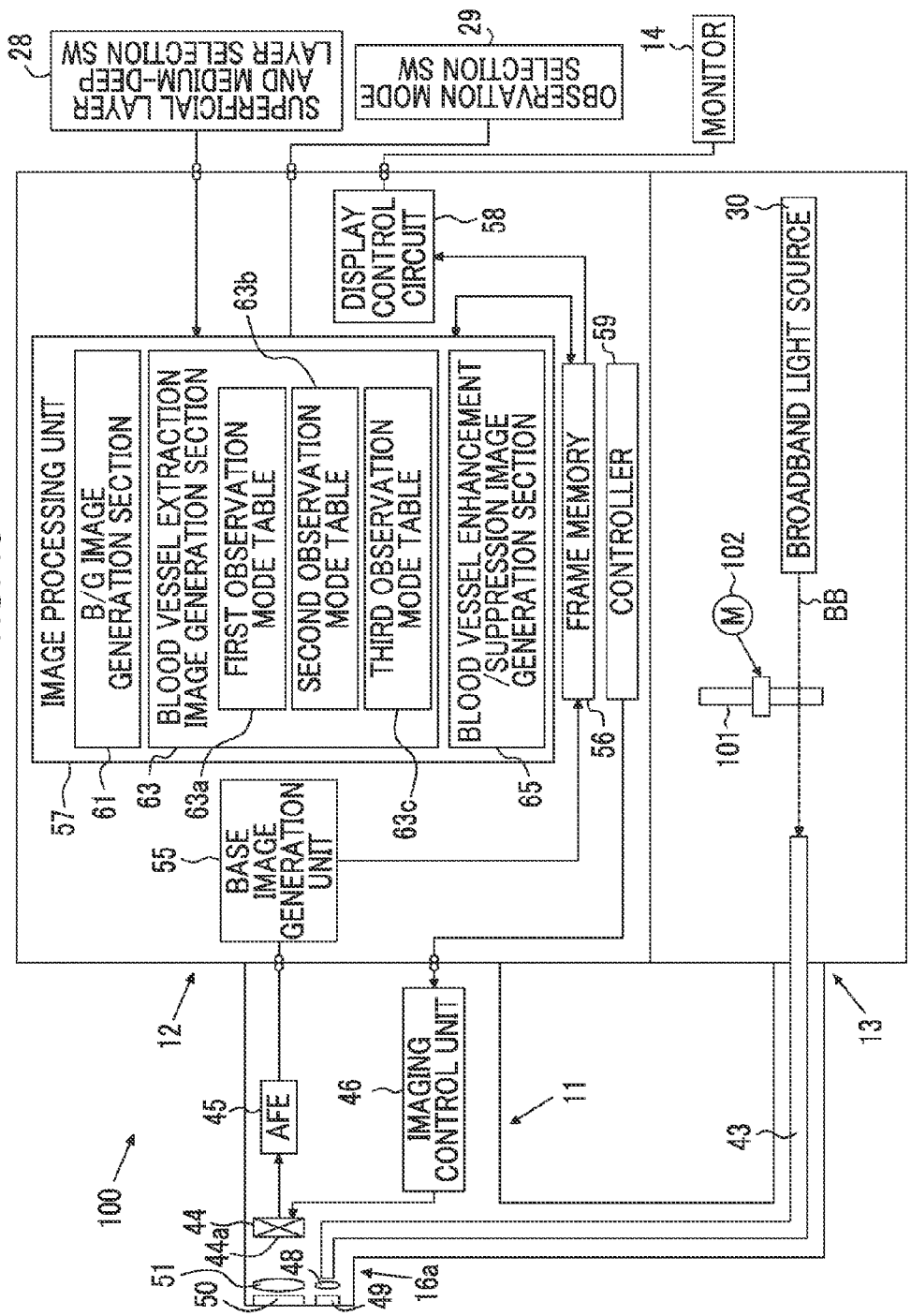
FIG. 15 is a block diagram showing the electrical configuration of an endoscope system of a second embodiment.

In the second embodiment of the present invention, unlike in the first embodiment in which two types of illumination light beams to illuminate a subject are simultaneously irradiated, two types of illumination light beams are separately irradiated in a sequential manner. Here, as two types of illumination light beams, blue narrowband light GN having a center wavelength of 415 nm and green narrowband light BN having a center wavelength of 540 nm are sequentially irradiated. Accordingly, in an electronic endoscope system 100 of the second embodiment, as shown in FIG. 15, a rotary filter 101 and a motor 102 for rotating the rotary filter 101 at the fixed speed are used to irradiate the blue narrowband light BN and the green narrowband light GN sequentially. In addition, in order to image the inside of the subject, a monochrome CCD 101 in which no color filter is provided is used instead of the color CCD 44.

Figure 16:
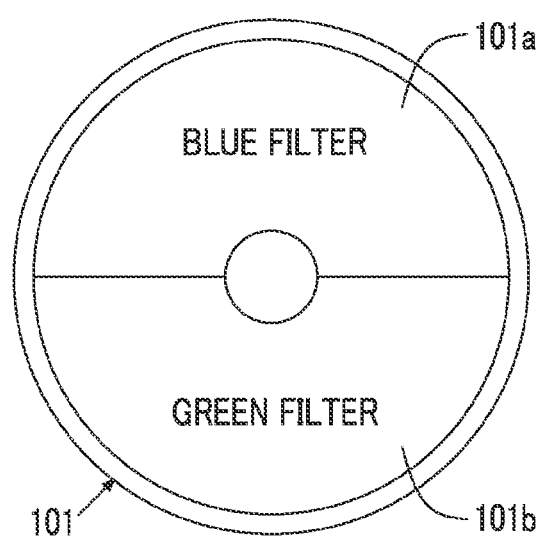
FIG. 16 is a schematic diagram of a rotary filter.

As shown in FIG. 16, in the rotary filter 101, a blue filter 101a, through which the blue narrowband light BN (having a wavelength region of 380 nm to 430 nm) having a center wavelength of 415 nm of the broadband light BB from the broadband light source 30 is transmitted, and a green filter 101b, through which the green narrowband light GN (having a wavelength region of 520 nm to 560 nm) having a center wavelength of 540 nm of the broadband light is transmitted, are provided in the circumferential direction. Therefore, the blue narrowband light BN and the green narrowband light GN are separately irradiated in a sequential manner toward the light guide 43 due to the rotation of the rotary filter 101.

The base image generation method and the B/G image generation method based on the sequential irradiation of the blue narrowband light BN and the green narrowband light GN described above are different from those in the first embodiment of the simultaneous irradiation method. Others in the second embodiment are the same as in the first embodiment. When generating a base image, a blue narrowband signal obtained when irradiating and capturing the blue narrowband light BN is assigned to the B and G channels for monitor display, and a green narrowband signal obtained when irradiating and capturing the green narrowband light GN is assigned to the R channel for monitor display, thereby generating the base image. When generating a B/G image, the B/G image is generated from the brightness ratio between the blue narrowband signal and the green narrowband signal.

In the embodiment described above, medium-deep blood vessels and superficial blood vessels are separated from each other using the B/G ratio. Instead of this, the blood vessels can also be separated using calculation values obtained by calculation using two or more color signals having different pieces of color information, such as a G/B ratio, a B−G difference, a G−B difference, a B/(B+G) ratio, a G/(B+G) ratio, a B/R ratio, an RIB ratio, a B−R difference, an R−B difference, and a RN ratio.

Figure 17A:
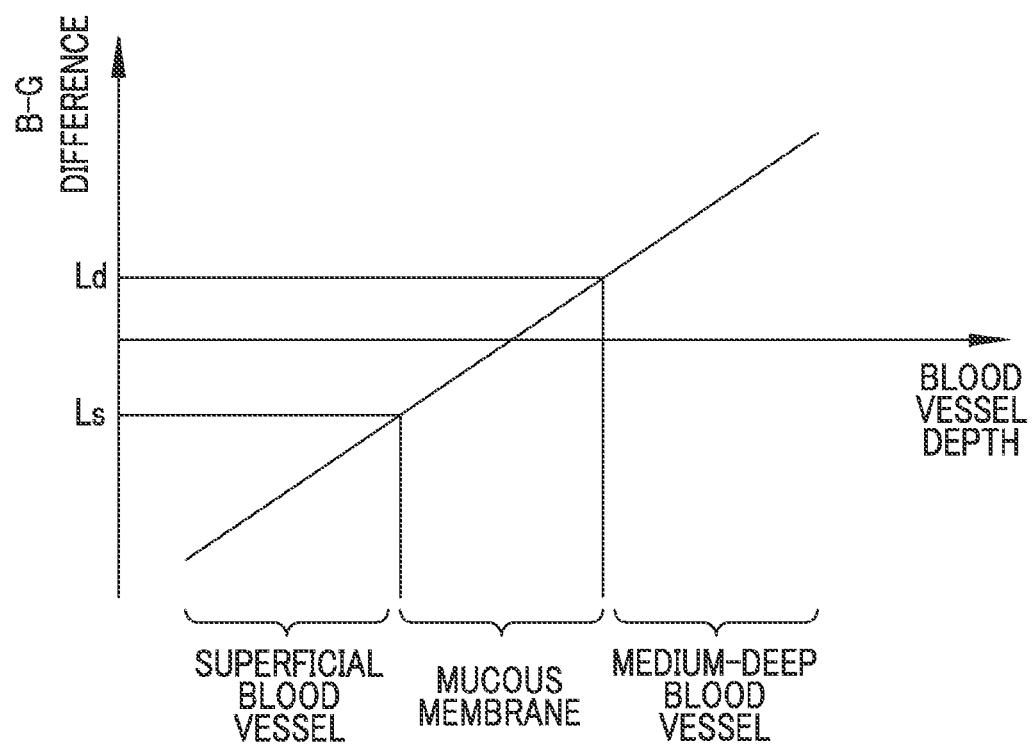
FIG. 17A is a graph showing the relationship between the blood vessel depth and the B−G difference that is stored in a first observation mode table.

As in the embodiment described above, the relationship between the calculated value and the blood vessel depth is stored in a plurality of tables corresponding to the first to third observation modes, and the boundary value of the calculated value indicating the boundary between the mucous membrane and the superficial blood vessel and the boundary value of the calculated value indicating the boundary between the mucous membrane and the medium-deep blood vessel differ depending on each table. For example, in the case of the B−G difference (a value obtained by subtracting the pixel value of the green signal from the pixel value of the blue signal), the relationship between the B−G difference and the blood vessel depth shown in FIG. 17A is stored in a table that is used in the first observation mode. Here, Ls indicates a B−G difference indicating the boundary between the mucous membrane and the superficial blood vessel, and Ld indicates a B−G difference indicating the boundary between the mucous membrane and the medium-deep blood vessel.

Figure 17B:
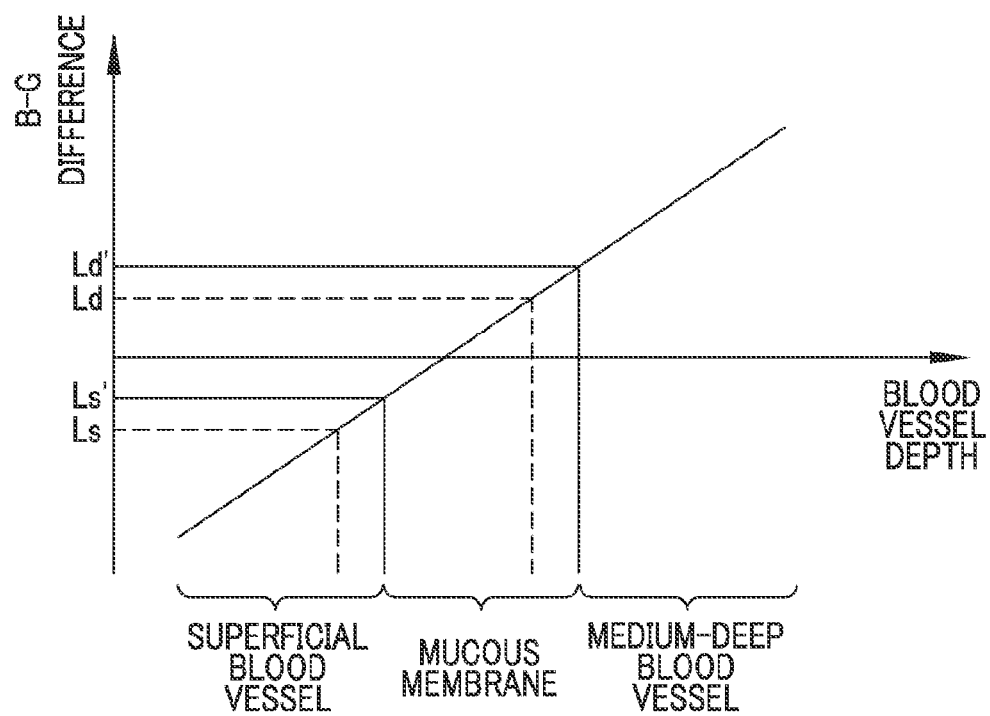
FIG. 17B is a graph showing the relationship between the blood vessel depth and the B−G difference that is stored in a second observation mode table.
Figure 17C:
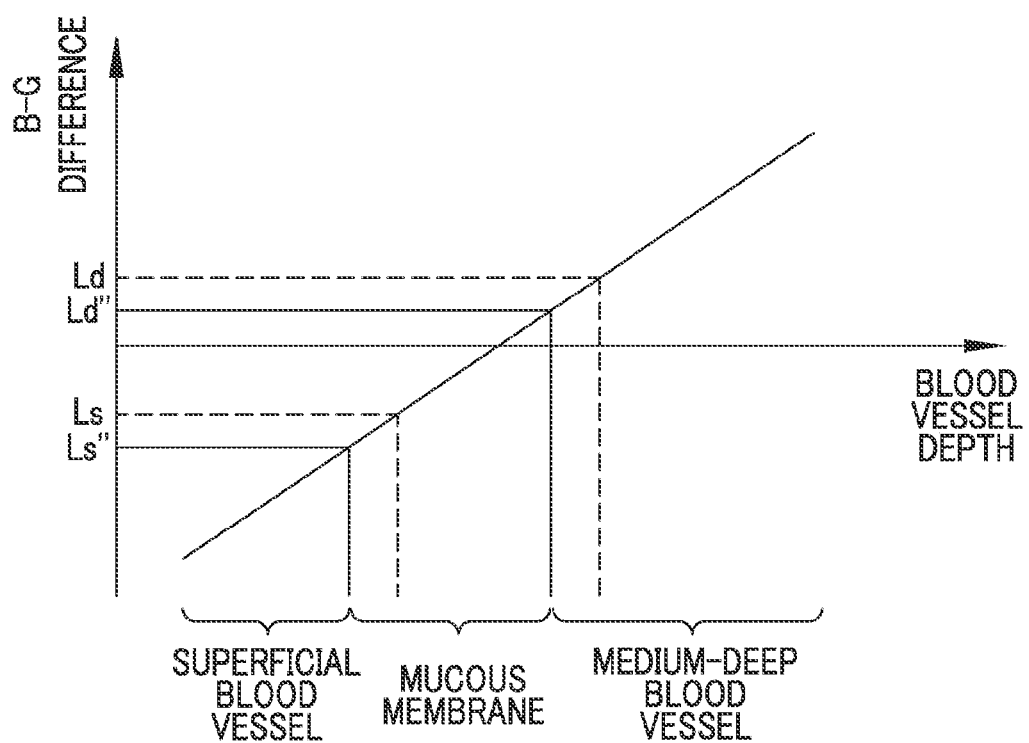
FIG. 17C is a graph showing the relationship between the blood vessel depth and the B−G difference that is stored in a third observation mode table.

On the other hand, the relationship between the B−G difference and the blood vessel depth shown in FIG. 17B is stored in a table that is used in the second observation mode. In this table, a B−G difference Ls' at the boundary between the mucous membrane and the superficial blood vessel is set to be larger than Ls, and a B−G difference Ld' at the boundary between the mucous membrane and the medium-deep blood vessel is set to be larger than Ld. In addition, the relationship between the B−G difference and the blood vessel depth shown in FIG. 17C is stored in a table that is used in the second observation mode. In this table, a B−G difference Ls" at the boundary between the mucous membrane and the superficial blood vessel is set to be smaller than Ls, and a B−G difference Ld" at the boundary between the mucous membrane and the medium-deep blood vessel is set to be smaller than Ld.

The G/B ratio is a value obtained by dividing the green signal by the blue signal, the G−B difference is a value obtained by subtracting the blue signal from the green signal, the B/(B+G) ratio is a value obtained by dividing the blue signal by the sum of the blue signal and the green signal, the G/(B+G) ratio is a value obtained by dividing the green signal by the sum of the blue signal and the green signal, the B/R ratio is a value obtained by dividing the blue signal by the red signal, the R/B ratio is a value obtained by dividing the red signal by the blue signal, the B−R difference is a value obtained by subtracting the red signal from the blue signal, the R−B difference is a value obtained by subtracting the blue signal from the red signal, and the B/Y ratio is a value obtained by dividing the green signal by the yellow signal (yellow signal is a signal having wavelength information of 500 nm to 700 nm).

What is claimed is:

1. An endoscope system, comprising:
   an electronic endoscope that comprises an illumination device for irradiating a subject with illumination light including a blue component and a green component and an image signal acquisition device for acquiring two or more color signals having different pieces of color information by receiving and imaging return light from the subject using an imaging element;
   a processor device that
      generates a multi-color image formed from calculated values obtained by performing predetermined calculation for each pixel using the two or more color signals; and
      generates at least one of a first layer blood vessel extraction image, which is obtained by extracting a first layer blood vessel at a specific depth from the multi-color image, or a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image; and
   a plurality of calculated value tables, which store a correlation between a mucous membrane, the first layer blood vessel, and the second layer blood vessel of the subject and the calculated values,
   wherein the processor further generates at least one of the first layer blood vessel extraction image or the second layer blood vessel extraction image by performing blood vessel extraction processing using a calculated value table corresponding to the set observation mode,
   the calculated value table is set for each of the plurality of observation modes,
   wherein in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value, and
   the first and second boundary values differ depending on each calculated value table.

2. The endoscope system according to claim 1,
   wherein the plurality of observation modes are modes for improving visibility of a blood vessel in a predetermined part of the subject, and
   each of the observation modes is set for each predetermined part.

3. The endoscope system according to claim 2, further comprising:
a blood vessel enhancement image or suppression image generation device for generating a first layer blood vessel enhancement image or suppression image, in which the first layer blood vessel is enhanced or suppressed, using the first layer blood vessel extraction image, or generating a second layer blood vessel enhancement image or suppression image, in which the second layer blood vessel is enhanced or suppressed, using the second layer blood vessel extraction image.

4. The endoscope system according to claim 3, further comprising:
a display device for displaying at least one of the first layer blood vessel enhancement image or suppression image or the second layer blood vessel enhancement image or suppression image.

5. The endoscope system according to claim 2,
wherein the illumination device simultaneously irradiates blue narrowband light and fluorescent light that is wavelength-converted by a wavelength conversion member using the blue narrowband light, as the illumination light, toward the subject, and
the image signal acquisition device images the subject, to which the blue narrowband light and the fluorescent light are irradiated simultaneously, using a color imaging element.

6. The endoscope system according to claim 2,
wherein the illumination device sequentially irradiates blue narrowband light and green narrowband light, as the illumination light, toward the subject, and
the image signal acquisition device images the subject sequentially using a monochrome imaging element whenever the blue narrowband light and the green narrowband light are sequentially irradiated.

7. The endoscope system according to claim 2,
wherein the color signals include a blue signal having information of a blue component and a green signal having information of a green component, and
the multi-color image is a B/G image having a B/G ratio obtained by dividing the blue signal by the green signal for each pixel.

8. The endoscope system according to claim 1, further comprising:
a blood vessel enhancement image or suppression image generation device for generating a first layer blood vessel enhancement image or suppression image, in which the first layer blood vessel is enhanced or suppressed, using the first layer blood vessel extraction image, or generating a second layer blood vessel enhancement image or suppression image, in which the second layer blood vessel is enhanced or suppressed, using the second layer blood vessel extraction image.

9. The endoscope system according to claim 8, further comprising:
a display device for displaying at least one of the first layer blood vessel enhancement image or suppression image or the second layer blood vessel enhancement image or suppression image.

10. The endoscope system according to claim 9,
wherein the illumination device simultaneously irradiates blue narrowband light and fluorescent light that is wavelength-converted by a wavelength conversion member using the blue narrowband light, as the illumination light, toward the subject, and
the image signal acquisition device images the subject, to which the blue narrowband light and the fluorescent light are irradiated simultaneously, using a color imaging element.

11. The endoscope system according to claim 9,
wherein the illumination device sequentially irradiates blue narrowband light and green narrowband light, as the illumination light, toward the subject, and
the image signal acquisition device images the subject sequentially using a monochrome imaging element whenever the blue narrowband light and the green narrowband light are sequentially irradiated.

12. The endoscope system according to claim 8,
wherein the illumination device simultaneously irradiates blue narrowband light and fluorescent light that is wavelength-converted by a wavelength conversion member using the blue narrowband light, as the illumination light, toward the subject, and
the image signal acquisition device images the subject, to which the blue narrowband light and the fluorescent light are irradiated simultaneously, using a color imaging element.

13. The endoscope system according to claim 8,
wherein the illumination device sequentially irradiates blue narrowband light and green narrowband light, as the illumination light, toward the subject, and
the image signal acquisition device images the subject sequentially using a monochrome imaging element whenever the blue narrowband light and the green narrowband light are sequentially irradiated.

14. The endoscope system according to claim 8,
wherein the color signals include a blue signal having information of a blue component and a green signal having information of a green component, and
the multi-color image is a B/G image having a B/G ratio obtained by dividing the blue signal by the green signal for each pixel.

15. The endoscope system according to claim 1,
wherein the illumination device simultaneously irradiates blue narrowband light and fluorescent light that is wavelength-converted by a wavelength conversion member using the blue narrowband light, as the illumination light, toward the subject, and
the image signal acquisition device images the subject, to which the blue narrowband light and the fluorescent light are irradiated simultaneously, using a color imaging element.

16. The endoscope system according to claim 1,
wherein the illumination device sequentially irradiates blue narrowband light and green narrowband light, as the illumination light, toward the subject, and
the image signal acquisition device images the subject sequentially using a monochrome imaging element whenever the blue narrowband light and the green narrowband light are sequentially irradiated.

17. The endoscope system according to claim 1,
wherein the color signals include a blue signal having information of a blue component and a green signal having information of a green component, and
the multi-color image is a B/G image having a B/G ratio obtained by dividing the blue signal by the green signal for each pixel.

18. The endoscope system according to claim 1,
wherein the color signals include a blue signal having information of a blue component and a green signal having information of a green component, and the multi-color image is a B/G image having a B/G ratio obtained by dividing the blue signal by the green signal for each pixel.

19. A processor device for an endoscope system including an electronic endoscope that irradiates a subject with illumination light including a blue component and a green component and acquires two or more color signals having different pieces of color information by receiving and imaging return light from the subject using an imaging element, comprising:

a multi-color image generation unit for generating a multi-color image formed from calculated values obtained by performing predetermined calculation for each pixel using the two or more color signals; and a blood vessel extraction image generation unit for generating at least one of a first layer blood vessel extraction image, which is obtained by extracting a first layer blood vessel at a specific depth from the multi-color image, or a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image, wherein the blood vessel extraction image generation unit includes a plurality of calculated value tables, which store a correlation between a mucous membrane, the first layer blood vessel, and the second layer blood vessel of the subject and the calculated values, and a blood vessel extraction image generation section that generates at least one of the first layer blood vessel extraction image or the second layer blood vessel extraction image by performing blood vessel extraction processing using a calculated value table corresponding to the set observation mode, the calculated value table is set for each of the plurality of observation modes, wherein in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value, and the first and second boundary values differ depending on each calculated value table.

20. An image processing method performed in an endoscope system including an electronic endoscope that irradiates a subject with illumination light including a blue component and a green component and acquires two or more color signals having different pieces of color information by receiving and imaging return light from the subject using an imaging element, the image processing method comprising:

generating a multi-color image formed from calculated values obtained by performing predetermined calculation for each pixel using the two or more color signals; and generating at least one of a first layer blood vessel extraction image, which is obtained by extracting a first layer blood vessel at a specific depth from the multi-color image, or a second layer blood vessel extraction image, which is obtained by extracting a second layer blood vessel at a position deeper than the first layer blood vessel from the multi-color image, by performing blood vessel extraction processing, which differs depending on each of a plurality of observation modes, on the multi-color image, wherein the blood vessel extraction processing generates at least one of the first layer blood vessel extraction image or the second layer blood vessel extraction image by using a calculated value table corresponding to the set observation mode, the calculated value table stores a correlation between a mucous membrane, the first layer blood vessel, and the second layer blood vessel of the subject and the calculated values, the calculated value table is set for each of the plurality of observation modes, in each of the calculated value tables, a calculated value indicating a boundary between the mucous membrane and the first layer blood vessel is stored as a first boundary value, and a calculated value indicating a boundary between the mucous membrane and the second layer blood vessel is stored as a second boundary value, and the first and second boundary values differ depending on each calculated value table.

* * * * *